US012569475B2

(12) United States Patent
Fathi et al.

(10) Patent No.: US 12,569,475 B2
(45) **Date of Patent: *Mar. 10, 2026**

(54) METHOD FOR ERADICATING HELICOBACTER PYLORI INFECTION IN PATIENTS REGARDLESS OF BODY MASS INDEX

(71) Applicant: RedHill Biopharma Ltd., Tel-Aviv (IL)

(72) Inventors: Reza Fathi, Oradell, NJ (US); Kely Lee Sheldon, Atlanta, GA (US)

(73) Assignee: RedHill Biopharma Ltd., Tel-Aviv (IL)

(*) Notice: Subject to any disclaimer, the term of this patent is extended or adjusted under 35 U.S.C. 154(b) by 68 days.

This patent is subject to a terminal disclaimer.

(21) Appl. No.: 18/532,876

(22) Filed: Dec. 7, 2023

(65) Prior Publication Data

US 2024/0100034 A1 Mar. 28, 2024

Related U.S. Application Data

(63) Continuation of application No. 16/869,199, filed on May 7, 2020, now Pat. No. 11,878,011.

(51) Int. Cl.

| | |
|---|---|
| ***A61K 31/4439*** | (2006.01) |
| ***A61K 9/20*** | (2006.01) |
| ***A61K 9/28*** | (2006.01) |
| ***A61K 31/43*** | (2006.01) |
| ***A61K 31/438*** | (2006.01) |

(52) U.S. Cl.

CPC ........ *A61K 31/4439* (2013.01); *A61K 9/2072* (2013.01); *A61K 9/28* (2013.01); *A61K 31/43* (2013.01); *A61K 31/438* (2013.01)

(58) Field of Classification Search

CPC .................................................. A61K 31/4439

See application file for complete search history.

(56) References Cited

U.S. PATENT DOCUMENTS

| | | | |
|---|---|---|---|
| 5,927,500 | A | 7/1999 | Godfrey et al. |
| 6,136,344 | A | 10/2000 | Depui et al. |
| 6,489,317 | B1 | 12/2002 | Borody |
| 6,605,303 | B1 | 8/2003 | Karehill et al. |
| 9,050,263 | B2 | 6/2015 | Fathi |
| 9,498,445 | B2 | 11/2016 | Fathi et al. |
| 9,603,806 | B2 | 3/2017 | Fathi et al. |
| 10,238,606 | B2 | 3/2019 | Fathi et al. |
| 2004/0213847 | A1 | 10/2004 | Matharu et al. |
| 2009/0028940 | A1 | 1/2009 | Jahagirdar et al. |
| 2009/0028941 | A1 | 1/2009 | Cowles et al. |
| 2009/0220611 | A1 | 9/2009 | Dargelas et al. |
| 2014/0227353 | A1 | 8/2014 | Fathi et al. |

FOREIGN PATENT DOCUMENTS

| | | | |
|---|---|---|---|
| CN | 101584681 | A | 11/2009 |
| CN | 101607086 | A | 12/2009 |
| CN | 101888828 | A | 11/2010 |
| CN | 102091084 | B | 5/2012 |
| EP | 1 803 450 | A1 | 7/2007 |
| JP | 2000128779 | A | 5/2000 |
| WO | 1996/024375 | A1 | 8/1996 |
| WO | 98/22117 | A1 | 5/1998 |
| WO | 98/40054 | A1 | 9/1998 |
| WO | 2005/048979 | A2 | 6/2005 |
| WO | 2007/077158 | A1 | 7/2007 |
| WO | 2009/017716 | A2 | 2/2009 |
| WO | 200913884 | A1 | 11/2009 |

OTHER PUBLICATIONS

Salcedo et al. (Treatment of Heliobacter pylori infection) (Year: 1998).*

Staying healthy (Probiotics may help to prevent diarrhea due to antibiotic use). (Year: 2012).*

Abdullahi et al., The Eradication of Helicobacter pylori is Affected by Body Mass Index (BMI); Apr. 29, 2008, Obes Surg (2008) 18:1450-1454.

Hall II, "Evolving Larger: Dosing Anti-Tuberculosis (TB) Drugs in an Obese World"; Current Pharmaceutical Design, 2015, 21, 000-000, pp. 1-4.

Heep et al., "Rifampin and Rifabutin Resistance Mechanism in Helicobacter pylori"; Antimicrobial Agents and Chemotherapy, Jun. 1999, vol. 43, No. 6, p. 1497-1499.

Horne et al., "Experience with Rifabutin Replacing Rifampin in the Treatment of Tuberculosis", Int J Tuberc Lung Dis. Nov. 2011; 15(11): 1485-i.

Kao et al., "Helicobacter pylori eradication by low-dose rifabutin triple therapy (RHB-105) is unaffected by high body mass index", GastroHep. 2021, 3: 426-434.

Longo et al., "The effect of obesity on antibiotic treatment failure: a historical cohort study", Pharmacoepidemiology and Drug Safety (2013), DOI: 10.1002/pds.3461.

Shah et al., "Helicobacter pylori infection treatment in the United States: clinical consequences and costs of eradication treatment failure", Expert Review of Gastroenterology & Hepatology, 2022, vol. 167, No. 4, pp. 341-357.

(Continued)

*Primary Examiner* — Sarah Alawadi

(74) *Attorney, Agent, or Firm* — GREENBERG TRAURIG, LLP

(57) ABSTRACT

A method of treating patients who are positive for *Helicobacter pylori* infection comprises determining that a first patient who is positive for *Helicobacter pylori* infection has a body mass index corresponding to normal weight or overweight; determining that a second patient who is positive for *Helicobacter pylori* infection has a body mass index corresponding to obese or extremely obese; and administering to both the first patient and the second patient, for 14 days, a rifabutin-based triple therapy consisting essentially of rifabutin, amoxicillin and omeprazole or an equivalent amount of a pharmaceutically acceptable salt thereof, wherein, after treatment is complete, there is no substantial difference in the efficacy of the treatment when the treatment is administered to the first patient or the second patient.

19 Claims, 2 Drawing Sheets

(56) References Cited

OTHER PUBLICATIONS

Sullam, "Rifabutin Therapy for Disseminated *Mycobacterium avium* Complex Infection", Clinical Infections Diseases, 1996;22 (Suppl 1) pp. S37-42.
Tissen et al., "Development of mini-tablets with 1 mm and 2 mm diameter", 2011, International Journal of Pharmaceutics, vol. 416, pp. 164-170 (Year: 2011).
Al-Dorzi et al., "Antibiotic therapy of pneumonia in the obese patient: dosing and delivery", Current Opinion; 2014 Wolters Kluwer Health; Lippincourt Williams & Wilkins; www.co-infectiousdiseases.com.
Barras et al., "Drug dosing in obese adults", Australian Prescriber, vol. 40, No. 5: Oct. 2017.
Cerqueira et al., "Cumulative Helicobacter pylori Eradication Therapy in Obese Patients Undergoing Gastric Bypass Surgery", Clinical Research; Obes Surg (2013) 23: 145-149.
Laudanno et al., "Helicobacter Pylori Eradication in Obese Patients Undergoing Bariatric Surgery", AGA Abstracts, 2017, Sa1189; S-247.
Lemus-Castellanos et al., "Population Pharmacokinetics of Clarithromycin in Mexican Hospitalized Patients with Respiratory Disease: Evidence for a Reduced Clearance", Research Article, International Journal of Pharmacology, 13 (1): 54-63, 2017.
McCafferty et al., "Obesity: Scope, Lifestyle Interventions, and Medical Management", Techniques in Vascular and Interventional Radiology, 2020.
Meng et al., "Comprehensive Guidance for Antibiotic Dosing in Obese Adults", Pharmacotherapy 2017;37 (11):1415-1431.
Pintar et al., "The need for a patient-tailored Helicobacter pylori eradication protocol prior to bariatric surgery", Journal of International Medical Research, 2018, vol. 46(7) 2696-2707.
RedHill Biopharma Press Release, "RedHill Biopharma Announces Standard-of-Care Eradication Data from the RHB-105 Phase III Study Further Supporting the Study's Positive Results".
RedHill Biopharma Press Release, "RedHill Biopharma Announces Confirmatory Phase III Study Initiated with RHB-105 (Talicia) for H.pylor Infection".
RedHill Biopharma Press Release, "RedHill Biopharma Successfully Meets Primary Endpoint in Phase III Study of RHB-105 for H.pylori Infection".
RedHill Biopharma Press Release, "RedHill Biopharma Announces Positive Top-Line Results from Confirmatory Phase 3 Study with TALICIA for H. pylori Infection".
"ERADICATE Hp2—Treating Helicobacter Pylori with RHB-105 Compared to Active Comparator (ERADICATE Hp2)", Trial record 1 of 1 for: NCT03198507, U.S. National Library of Medicine, 2020 <<https://clinicaltrials.gov/ct2/show/NCT03198507?term=NCT03198507&draw=2&rank=1>>.
"ERADICATE Hp—Treating Helicobacter Pylori with RHB-105 (Eradicate Hp)", Trial record 1 of 1 for: NCT01980095; U.S. National Library of Medicine, 2019 <<https://clinicaltrials.gov/ct2/show?NCT01980095?term=NCT01980095&draw=2&rank=1>>.
"The impact of obesity on drug prescribing in primary care", British Journal of General Practice, Oct. 2005, pp. 743-749.
Yasgur, "Antibiotic Failure: A Weighty Issue in Patients with Obesity", MPR, retrieved Apr. 27, 2020 <<https://www.empr.com/home/features/antibiotic-failure-a-weighty-issue-in-patients-with-obesity/>>.
Sierra et al., "Ideal treatment for Helicobacter pylori: A systematic review", Revista de Gastroenterologia de Mexico, 2014; 79(1): 28-49.
D.A. Charkevich, "Farmakologiya", Pharmacology textbook, 9th ed. 2006, p. 66.
ERADICATE Hp—Treating Helicobacter Pylori with RHB-105 (ERADICATE Hp), ClinicalTrials.gov, NCT01980095, Nov. 8, 2013.
ERADICATE Hp2—Treating Helicobacter Pylori with RHB-105 Compared to Active Comparator (ERADICATE Hp2), ClinicalTrials.gov, NCT03198507, Jun. 26, 2017.
RedHill Biopharma Press Release; "RedHill Biopharma Successfully Meets Primary Endpoint in Phase III Study of RHB-105 for H.pylori Infection", Jun. 15, 2015.
RedHill Biopharma Press Release; "RedHill Biopharma Announces Standard-of-Care Eradication Data from the RHB-105 Phase III Study Further Supporting the Study's Positive Results", Sep. 8, 2015.
RedHill Biopharma Press Release, "RedHill Announces Positive Top-Line Results from Confirmatory Phase 3 Study with TALICIA for H.pylori Infection", Dec. 3, 2018.
RedHill Biopharma Press Release, "RedHill Biopharma Announces Confirmatory Phase III Study Initiated with RHB-105 (Talicia) for H. pylori Infection", Jun. 15, 2017.
Meng et al., "Comprehensive Guidance for Antibiotic Dosing in Obese Adults", Pharmacotherapy, vol. 37, No. 11, 2017, pp. 1415-1431.
Laudanno et al., "Helicobacter Pylori Eradication in Obese Patients Undergoing Bariatric Surgery", Sa1189, AGA Abstracts 2017.
Barrar et al., "Drug dosing in obese adults"; Australian Prescriber, vol. 40, No., 5, Oct. 2017, pp. 189-193.
Yasgur, "Antibiotic Failure: A Weighty Issue in Patients with Obesity", MPR, Jul. 1, 2013, pp. 1-5.
Cerqueira et al., "Cumulative Helicobacter pylori Eradication Therapy in Obese Patients Undergoing Gastric Bypass Surgery", Obes Surg (2013) 23: 145-149.
Abdullahi et al., "The Eradication of Helicobacter pylori is Affected by Body Mass Index (BMI)", Obes Surg (2008) 18: 1450-1454.
Gibbs et al., "The impact of obesity on drug prescribing in primary care", British Journal of General Practice, Oct. 2005, pp. 743-749.
Extended European Search Report from European Patent Application No. 14751025.9 dated Sep. 13, 2016.
Omerprazole Delayed-Release Capsules; Official Monographs/Omeprazole, USP 35, pp. 4113-4115; 2014 U.S. Pharmacopela National Formulay, Official Dec. 1, 2014 to Apr. 30, 2015.
Abbreviated Drug Class Review: Proton Pump Inhibitors, VHA Pharmacy Benefits Management Strategic Healthcare Group and the Medical Advisory Panel, Aug. 2006.
Borody, T. J. et al., "Efficacy and saftey of rifabutin-containing 'rescue therapy' for resistant Helicobacter pylori infection", Alimentary Pharmacology & Therapeutics 2005, p. 481-488.
Krishna, G. et al., "Evaluation of the pharmacokinetics of posaconazole and rifabutin following co-administration to healthy men", Current Medical Research and Opinion 2007, vol. 23 No. 3, p. 545-552.
Lozniewski A. et al., "Gastric diffusion of antibiotics used against Helicobacter pylori", International Journal of Antimicrobial Agents, 1998, p. 181-193.
Goddard, Andrew F. et al., "In Vitro Assessment of Gastric Mucosal Transfer of Anti-Helicobacter Therapeutic Agents", Antimicrobial Agents and Chemotherapy, Jun. 1997, p. 1246-1249.
Mainz, Dagmar et al., "Pharmacokinetics of lansoprazole, amoxicillin and clarithromycin after simultaneous and single administration", Journal of Antimicrobial Chemotherapy 2002, 50, p. 699-706.
Robinson, M., "Review article: the pharmacodynamics and pharmacokinetics of proton pump inhibitors—overview and clinical implications", Aliment Pharmacal. Ther. 2004, 20 (Suppl. 6), p. 1-10.
AGA (American Gastroenterological Association), "American Gastroenterological Association Medical Position Statement: Evaluation of Dyspepsia", Gastroenterology (2005), 129:1753-1755.
Akada, Junko K. et al., "In Vitro Anti-Helicobacter pylori Activities of New Rifamycin Derivatives, KRM-1648 and KRM-1657", Antimicrob Agents and Chemotherapy (1999), 43(5):1072 1076.
Dr. Reddys Laboratories Inc., Amoxicillin Capsules and Amoxicillin Powder, for Suspension, Package Insert (May 2012).
Apseloff, Glen M.D., "Severe neutropenia among healthy volunteers given rifabutin in clinical trials", Clinical Pharmacology and Therapeutics (Dec. 2003), 74:591-592.
Axon, A.T.R., "Campylobacter pylori-therapy review", Scand. J. Gastroenterol (1989), 24 Suppl. 160:35-38.
Axon, Anthony et al., "Helicobacter gastroduodenitis: a serious infectious disease", British Medical Journal. (1997), 314:1430-1431.

(56) References Cited

OTHER PUBLICATIONS

Barzilay, Ezra J., Chapter 3: Infectious Diseases Related to Travel, IN:2012 Yellow Book—Travelers' Health—CDC. (2011), New York: Oxford University Press Inc.
Bazzoli, Franco et al., "Short-term low-dose triple therapy for the eradication of Helicobacter pylori", Eur. J. Gastroenterol Hepatol. (1994), 6:773-777.
Beales, Ian LP., "Efficacy of Helicobacter pylori eradication therapies: a single centre observational study", BioMed Central, Gastroenterology (2001), 1:7.
Behrens, Rolf et al., "Dual versus triple therapy of Helicobacter pylori infection: results of a multicentre trial", Arch Dis Child (Jul. 1999), 81:68-70.
Bock, H. M.D. et al., "Rifabutin-based triple therapy after failure of Helicobacter pylori eradication treatment: preliminary experience", J. Clin. Gastroenterol. (2000), 31:222-225.
Borody, T.J et al., "Symptoms improve after the eradication of gastric Campylobacter pyloridis", Medical J. Australia. (1987), 146:450-451.
Borody, T.J. and Brandi S, Andrews P. et al., H. Pylori eradication failure (EF)—further treatment possibilities, Gastroenterology. (1992), 102:A43.
Borody, T.J. et al., "Efficacy and safety of rifabutin-containing 'rescue therapy' for resistant Helicobacter pylori infection"; Aliment Pharmacology Therap. (2006) 23:481-488.
Brogden, Rex N. et al., "A review of its antimicrobial activity, pharmacokinetic properties and therapeutic efficacy", Drug Evaluation., Drugs (1994), 47:983-1009.
Broutet, N. et al. "Risk factors for failure of Helicobacter pylori therapy—results of an individual data analysis of 2751 patients", Aliment Pharmacol. Therap. (2003), 17:99-109.
Burman, William et al., "Acquired rifamycin resistance with twice-weekly treatment of HIV-related tuberculosis", Am. J. Respir. Crit. Care Med. (2006), 173:350-356.
Canducci, F. et al., "Rifabutin-based Helicobacter pylori eradication 'rescue therapy'", Aliment Pharmacol. Ther. (Jan. 2001), 15:143.
Cardenas, Victor M. et al., "Iron deficiency and Helicobacter pylori infection in the United States", Am. J. Epidemiology (2006), 163:127-134.
Cardenas, Victor M. et al., Helicobacter pylori Eradication and Its Effect on Iron Stores: A Reappraisal, J. Infect. Dis. (2006), 194:714.
Chey, William D. et al., "Noninvasive Helicobacter pylori testing for the "test-and-treat" strategy: A decision analysis to assess the effect of past infection on test choice", Arch. Intern. Med. (2001), 161:2129-2132.
Chey, William D. et al., "American College of Gastroenterology guideline on the management of Helicobacter pylori infection", Am. J. Gastroenterol. (2007), 102:1808-1825.
D'Elios, Mario M. et al., "Helicobacter pylori: usefulness of an empirical fourth-line rifabutin-based regimen", Expert Rev. Gastroenterol Hepatol. (2012), 6:437-439.
De Francesco, Vincenzo et al., Worldwide H. pylori Antibiotic Resistance: a Systematic Review, J. Gastrointestin. Liver Dis. (2010), 19:409-414.
Dholakia, K.R. et al., "Vitamin B12 deficiency and gastric histopathology in older patients", World J. Gastroenterol. (2005), 11(45):7078-7083.
DuBois, Suja et al., "Iron-deficiency anemia and Helicobacter pylori infection: a review of the evidence", Am. J. Gastroenterol. (2005), 100:453-459.
Duck, William M. et al., "Antimicrobial resistance incidence and risk factors among Helicobacter pylori infected persons, United States", Emerg. Infect. Dis. (2004), 10:1088-1094.
Ekstrom, Anna Mia et al., "Helicobacter pylori in gastric cancer established by CagA immunoblot as a marker of past infection", Gastroenterology. (2010), 121(4):784-791.
Fiorini, G. et al., "Culture-Based Selection Therapy for Patients Who Did Not Respond to Previous Treatment for Helicobacter pylori Infection", Clin. Gastroenterol. Hepatol. (Dec. 22, 2012), pil: S1542-3565(12)01507-8. doi: 10.1016/j.cgh.2012.12.007. [Epub ahead of print].
Ford, Alexander C. et al., "Epidemiology of Helicobacter pylori infection and Public Health Implications", Helicobacter. (2010), 15 (Suppl. 1): 1-6.
Gisbert, J.P. et al., "Review article: Helicobacter pylori 'rescue' regimen when proton pump inhibitor-based triple therapies fail", Aliment Pharmacol. Ther. (2002), 16:1047-1057.
Gisbert, J.P. et al., "Third-line rescue therapy with levofloxacin is more effective than rifabutin rescue regime after two Helicobacter pylori treatment failures", Aliment Pharmacol. Ther. (2006), 24:1469-1474.
Gisbert, J.P., "Rescue" regimens after Helicobacter pylori treatment failure, World J. Gastroenterol. (2008), 14 (35):5385-5402.
Gisbert, J.P., "Rescue Therapy for Helicobacter pylori Infection 2012", Gastroenterol Res. Pract. (2012a), epub. 974594.
Gisbert, J.P. et al., "Fourth-line rescue therapy with rifabutin in patients with three Helicobacter pylori eradication failures", Aliment Pharmacol. Ther. (2012c), 35(8):941-947.
Glocker, Erik et al., "Characterization of rifampicin-resistant clinical Helicobacter pylori isolates from Germany", Journal of Antimicrobial Chemotherapy. (2007), 59:874-879.
Glupczynski, Y. et al., "Lack of antibiotic compliance in patients treated for Campylobacter pylori-associated gastritis", Am. J. Gastroenterol. (1989), 84:1125-1126.
Goddard, Andrew F. et al., "Effect of omeprazole on the distribution of metronidazole, amoxicillin, and clarithromycin in human gastric juice", Gastroenterology. (1996), 111:358-367.
Godoy, Anita Paula Ortiz et al., "Analysis of antimicrobial susceptibility and virulence factors in Helicobacter pylori clinical isolates", BioMed Central, Gastroenterol. (2003), 11:3-20.
Gonzalez, Pedro Carro et al., "Efficacy of rifabutin-based triple therapy in Helicobacter pylori infected patients after two standard treatments", J. Gastroenterol. Hepatol. (2007), 22,60-63.
Graham, David Y. et al., "Seroepidemiology of Helicobacter pylori infection in India, Comparison of developing and developed countries"; Dig. Dis. Sciences. (1991), 36:1084-1088.
Graham, Kathleen S. et al., "Variability with omeprazole-amoxicillin combinations for treatment of Helicobacter pylori infection", Am. J. Gastroenterol. (1995), 90:1415-1418.
Graham, David Y., "Editorial: Can therapy ever be denied for Helicobacter pylori infection?", Gastroenterology. (1997a), 113:S113-S117.
Graham, David Y., "Helicobacter pylori infection in the pathogenesis of duodenal ulcer and gastric cancer: a model", Gastroenterology. (1997b), 113:1983-1991.
Graham, David Y., "Efficient identification and evaluation of effective Helicobacter pylori therapies", Clin. Gastroenterol Hepatol. (2009), 7:145-148.
Graham, David Y. et al., "Clinical practice: diagnosis and evaluation of dyspepsia", J. Clin. Gastroenterol. (2010a), 44:167-172.
Graham, David Y., "Helicobacter pylori eradication therapy research: ethical issues and description of results", Clin. Gastroenterol Hepatol. (2010b), 8:1032-1036.
Graham, David Y. et al., "Helicobacter pylori therapy demystified", Helicobacter. (2011), 16:343-345.
Graham, David Y. et al., "Guide regarding choice of second-line therapy to obtain a high cumulative cure rate", Helicobacter. (2012), 17:243-245.
Grayson, M.L. et al., "Effect of varying pH on the susceptibility of Campylobacter pylori to antimicrobial agents", Eur. J. Clin. Microbiol. Infect. Dis. (1989), 8:888-889.
Harford, William et al., "Double-blind, multicenter evaluation of lansoprazole and amoxicillin dual therapy for the cure off Helicobacter pylori infection", Helicobacter (1996), 1:243-250.
Heep, Markus et al., "Rifampin and rifabutin resistance mechanism in Helicobacter pylori", Antimicrobial Agents and Chemother. (1999), 43:1497-1499.
Kelleher, P. et al., "Uveitis associated with rifabutin and macrolide therapy for *Mycobacterium avium* intracellulare infection in AIDS patients", Genitourin Med. (1996), 72:419-421.

(56) References Cited

OTHER PUBLICATIONS

Kim, Jung Mogg et al., "Comparison of primary and secondary antimicrobial minimum inhibitory concentrations for Helicobacter pylori isolated from Korean patients", Int. J. Antimicrob Agents. (2006), 28:6-13.
Kim, Seung Young et al., "Effectiveness of three times daily lansoprazole/amoxicillin dual therapy for Helicobacter pylori infection in Korea", Br. J. Clin. Pharmacol. (2011), 73:1:140 143.
Kita, Tomoko et al., "CYP2C19 genotype related effect of omeprazole on intragastric pH and antimicrobial stability", Pharm. Res. (2001), 18:615-21.
Kumala, Widyasari et al., "Patterns of Helicobacter pylori isolate resistance to fluoroquinolones, amoxicillin, clarithromycin and metronidazole", Southeast Asian J. Trop Med Public Health. (2006), 37:970-974.
Kunin, Calvin M., "Antimicrobial activity of rifabutin", Clin. Infect Dis. (1996), 2 (Suppl 1) S3-14.
Lee, Yi-Chia et al., "The benefit of mass eradication of Helicobacter pylori infection: a community-based study of gastric cancer prevention", Gut. (2013), 62(5):676-82, doi:10.1136/gutjnl-2012-302240, Epub. (Jun. 14, 2012).
Li, Albert P. et al., "Primary human hepatocytes as a tool for the evaluation of structure-activity relationship in cytochrome P450 induction potential of xenobiotics: evaluation of rifampin, rifapentine, and rifabutin", Chemico-Biological Interactions (1997), 107:17-30.
Li, Jiehui et al., "Relapse and acquired rifampin resistance in HIV infected patients with tuberculosis treated with rifampin- or rifabutin-based regimens in New York City, 1997-2000", Clin. Infect. Dis. (2005), 41:83-91.
Luther, Jay et al., "Empiric quadruple vs. triple therapy for primary treatment of Helicobacter pylori infection: systematic review and meta-analysis of efficacy and tolerability", Am. J. Gastroenterol. (2010), 105:65-73.
Maconi, Giovanni et al., "Predictors of long-term outcome of functional dyspepsia and duodenal ulcer after successful Helicobacter pylori eradication-a 7-year follow-up study", European. J. Gastroenterol Hepatol. (2009), 21(4):387-393.
Malfertheiner, P. et al., "Current European concepts in the management of helicobacter pylori infection—the Maastricht consensus report", The European Helicobacter pylori study group (EHPSG) Eur. J. Gastroenterol Hepatol. (1997), 9:12.
Malfertheiner, P., Management of H. pylori infection: Maastricht III—2005.
Malfertheiner, Peter et al., "Guidelines for the Management of Helicobacter pylori Infection", Business Review: European Gastroenterology Review (2005), 59-60, 998-999.
Malfertheiner, P. et al., "Helicobacter pylori eradication with a capsule containing bismuth subcitrate potassium, metronidazole, and tetracycline given with omeprazole versus clarithromycin-based triple therapy: a randomised, open-label, non-inferiority, phase 3 trial", The Lancet. (2011), 377:905-913.
Malfertheiner, Peter et al., "Management of Helicobacter pylori infection—the Maastricht IV/Florence Consensus report", Gut. (2012), 61:646-664.
Marshall, Barry J. et al., "Prospective double-blind trial of duodenal ulcer relapse after eradication of Campylobacter pylori", The Lancet. (Dec. 1988), 24/31, 2 (8626-8627):1437-1342.
Marshall, B. J., "Treatment strategies for Helicobacter pylori infection", Gastroenterol Clin. North Am. (1993), 22:183-198.
Mcnulty, Cliodna A. M. et al., "Campylobacter pyloridis and associated gastritis: investigator blind, placebo controlled trial of bismuth salicylate and erythromycin ethylsuccinate", British Medical Journal (1986), 293:645-649.
Megraud, F., "H pylori antibiotic resistance: prevalence, importance, and advances in testing", Gut. (2004), 53:1374-1384.
Megraud, Francis et al., "Helicobacter pylori resistance to antibiotics in Europe and its relationship to antibiotic consumption", Gut. (2013), 62:34-42.
Miehlke, S. et al., "Randomized trial of rifabutin-based triple therapy and high-dose dual therapy for rescue treatment of Helicobacter pylori resistant to both metronidazole and clarithromycin", Aliment Pharmacol. Ther. (2006), 24:395 403.
Miehlke, Stephan et al., "One-week once-daily triple therapy with esomeprazole, moxifloxacin, and rifabutin for eradication of persistent Helicobacter pylori resistant to both metronidazole and clarithromycin", Helicobacter. (2008), 13:69-74.
Moayyedi, P. et al., "Eradication of Helicobacter pylori for non-ulcer dyspepsia (Review)", The Cochrane Database of Systematic Reviews. (2006), 2:1-40.
MYCOBUTIN® (rifabutin) Capsules, Package Insert, (Jan. 2010), Pharmacia and Upjohn Company.
Navarro-Jarabo, Jose M. et al., "Efficacy of rifabutin-based triple therapy as second-line treatment to eradicate Helicobacter pylori infection", BioMed Central, Gastroenterol. (2007), 7:31.
NCI. Surveillance Epidemiology and End Results, SEER Stat Fact Sheet: Stomach, http://seer.cancer.gov/statfacts/html/stomach.html, Accessed Mar. 2013.
Oderda, G. et al., "Campylobacter pylori gastritis: long term results of treatment with amoxycillin", Arch. Dis. Child. (1989), 64:326-329.
OMECLAMOX-PAK™ (omeprazole, clarithromycin, amoxicillin) Kit, Package Insert, (Feb. 2012), Pernix Therapeutics.
Perri, A. et al., " Treatment of antibiotic-resistant Helicobacter pylori Infection", The New England Journal of Medicine (1998), 33:53.
Perri, F. et al., "Rifabutin-based 'rescue therapy' for Helicobacter pylori infected patients after failure of standard regimens", Aliment Pharmacol. Ther. (2000), 14:311 316.
Perri, Francesco et al., "Randomized study of two "rescue" therapies for Helicobacter pylori-infected patients after failure of standard triple therapies", Am. J. Gastroenterol. (2001), 96:58-62.
Perucca, E. et al., Comparative effects of rifabutin and rifampicin on hepatic microsomal enzyme activity in normal subjects, Eur. J. Clin. Pharmacol. (1988), 34:595 599.
PREVPAC® (lansoprazole, amoxicillin and clarithromycin) Kit, Package Insert, (Oct. 2009), Takeda Pharmaceuticals America.
PRILOSEC® (omeprazole) Delayed-Release Capsules and PRILOSEC® (omeprazole magnesium) for Delayed-Release Oral Suspension, Package Insert, (May 2013), AstraZeneca.
PROTONIX® (pantoprazole sodium) Tablet, Delayed Release and PROTONIX® (pantoprazole sodium) Granule, Delayed Release, Package Insert, (Oct. 2012), Wyeth.
Qasim, Asghar et al., "Rifabutin- and furazolidone-based Helicobacter pylori eradication therapies after failure of standard first- and second-line eradication attempts in dyspepsia patients", Aliment Pharmacol. Ther. (2005), 21:91-96.
Reinach, Benedetta et al., "Comparative effects of rifabutin and rifampicin on cytochromes P450 and UDP- glucuronosyl-transferases expression in fresh and cryopreserved human hepatocytes", Chem. Biol. Interact. (1999), 121:37-48.
Rimbara, Emiko et al., "Optimal therapy for Helicobacter pylori infections", Nature Reviews Gastroenterology & Hepatology (2011), 8:79-88.
Ronchera, C. L. et al., "Pharmacokinetic interaction between high-dose methotrexate and amoxicillin", Ther. Drug Monit. (1993), 15:375-379.
Salazar, Cesar O. et al., "Greater than 95% success with 14-day bismuth quadruple anti-Helicobacter pylori therapy: a pilot study in US Hispanics", Helicobacter. (2012), 17:382-390.
Salcedo, Julio A. et al., "Treatment of Helicobacter pylori infection", Arch. Intern. Med. (1998), 158:842-851.
Schwartz, H. et al, "Triple versus dual therapy for eradicating Helicobacter pylori and preventing ulcer recurrence: a randomized, double-blind, multicenter study of lansoprazole, clarithromycin, and/or amoxicillin in different dosing regimens", Am. J. Gastroenterol. (1998), 93:584-590.
Selgrad, Michael et al., "Clinical Aspects of Gastric Cancer and Helicobacter pylori—Screening, Prevention, and Treatment", Helicobacter, (2010), 15 (Suppl. 1), 40-45.
Shafran, Stephen D. et al., "A comparison of two regimens for the treatment of *Mycobacterium avium* complex bacteremia in AIDS: rifabutin, ethambutol, and clarithromycin versus rifampin, ethambutol,

(56) References Cited

OTHER PUBLICATIONS clofazimine, and ciprofloxacin", Canadian HIV Trials Network Protocol 010 Study Group. N. Engl. J. Med. (1996), 8 335:377-383.
Shirai, Naohito et al., "Dual therapy with high doses of rabeprazole and amoxicillin versus triple therapy with rabeprazole, amoxicillin, and metronidazole as a rescue regimen for Helicobacter pylori infection after the standard triple therapy", Eur. J. Clin. Pharmacol. (2007), 63:743-749.
Suzuki, Shoji et al., "Past rifampicin dosing determines rifabutin resistance of Helicobacter pylori", Digestion. (2009), 79:1-4.
Talley, Nicholas J., "Guidelines for the management of dyspepsia", Am. J. Gastroenterol. (2005), 100:2324-2337.
Thyagarajan, S.P., et al., "Geographical difference in antimicrobial resistance pattern of Helicobacter pylori clinical isolates from Indian patients: Multicentric study", J. Gastroenterol. Hepatol. (2003), 18:1373-1378.
Toracchio, S. et al., "Rifabutin based triple therapy for eradication of H. pylori primary and secondary resistant to tinidazole and clarithromycin", Dig. Liver. Dis. (2005), 37:33-38.
Tseng, Alice L. et al., "Rifabutin-associated uveitis", Ann. Pharmacother. (1995), 29:1149-1155.
Tsuchiya, Mamiko et al., "Helicobacter pylori urease inhibition by rabeprazole, a proton pump inhibitor", Biol. Pharm. Bull. (Aug. 1995), 18 (8):1053-1056.
Unge, P. et al., "Does omeprazole improve antimicrobial therapy directed towards gastric Campylobacter pylori in patients with antral gastritis?", A pilot study. Scand. J. Gastroenterol. Suppl. (1989), 167:49-54.
Van Der, Poorten D. et al. "The effectiveness of rifabutin triple therapy for patients with difficult to eradicate Helicobacter pylori in clinical practice", Aliment Pharmacol. Ther. (2007), 26:1537-1542.
Walsh, John H. et al., "The treatment of Helicobacter pylori infection in the management of peptic ulcer disease", New Eng. J. Med. (1995), 333:984-991.
Wannmacher, Lennita, "Review of the evidence for H. pylori treatment regimens", Section 17.1 (Review)—Adults and Children. 18th Expert Committee on the Selection and Use of Essential Medicines. (2011), World Health Organization.
World Health Organization, "Treatment of Tuberculosis Guidelines", 4th edition (2010), 85.
Wong, B. C. Y. et al., "Comparison of lansoprazole-based triple and dual therapy for treatment of Helicobacter pylori-related duodenal ulcer: an Asian multicentre double-blind randomized placebo controlled study", Aliment Pharmacol. Ther. (2000), 14:217 224.
Wong, W. M. et al., "Randomized controlled study of rabeprazole, levofloxacin and rifabutin triple therapy vs. quadruple therapy as second-line treatment for Helicobacter pylori infection", Aliment. Pharmacol. Ther. (2003), 17: 553-560.
PCT International Search Report and the Written Opinion of the International Searching Authority dated May 16, 2014 (11 pages).
Blaschke, Terrence F. et al., "The Clinical Pharmacokinetics of Rifabutin", Clinical Infectious Diseases, 1996: 22 (Suppl. 1):S15-22.
Gisbert, J. P. et al., "Review Article: Rifabutin in the Treatment of Refractory Helicobacter Pylori Infection", Aliment Pharmacal. Ther. 2012, www.medscape.com, 35(2), p. 209-221.
Dubois, Andre et al., "Transient and Persistent Experimental Infection of Nonhuman Primates with Helicobacter Pylori: Implications for Human Disease", Infection and Immunity, Aug. 1996, p. 2885-2891.
Tariq et al. (Reevalution of the Efficacy of First Line Regimen for Helicobacter pylori) Jan. 2020.

* cited by examiner

METHOD FOR ERADICATING HELICOBACTER PYLORI INFECTION IN PATIENTS REGARDLESS OF BODY MASS INDEX

CROSS-REFERENCE TO RELATED APPLICATIONS

This application is a continuation of U.S. patent application Ser. No. 16/869,199, filed May 7, 2020, which is incorporated by reference in its entireties for all purposes.

BACKGROUND

Gastric bypass and other weight-loss surgeries—known collectively as bariatric surgery, remain effective therapies for patients with morbid obesity. They have been shown to be safe and adequate in inducing sustainable and important weight loss. Bariatric surgeons often advocate preoperative *Helicobacter pylori* (*H. pylori*) testing and eradication because of the increased risk of postoperative ulcers and foregut symptoms in *H. pylori*-positive patients. Typically, prior to bariatric surgery, a patient is tested to see if they harbor a *H. pylori* infection. If the test comes back positive, the patient will have to be treated prior to receiving surgery, delaying their surgery by many months. If the patient's initial treatment for eradicating *H. pylori* infection is not effective, then that patient will have to try a different therapy, even further delaying their bariatric surgery. Recent evidence suggests patient body mass index (BMI) may contribute to the failure of empiric triple *H. pylori* therapy and concomitant quadruple *H. pylori* therapy. Physiologic alterations seen in obesity commonly impact the pharmacokinetics (PK) and pharmacodynamics (PD) of antibiotics typically resulting in suboptimal dosing of drugs and requiring dose modification to achieve efficacy.

SUMMARY OF THE INVENTION

Surprisingly we have found that the treatment effect observed, eradication of *H. pylori* infection, when a method of the present invention is carried out with a rifabutin-based *H. pylori* therapy, is substantially equivalent (i.e., no substantial difference) in adults regardless of their BMI category.

In one aspect, a method of treating patients who are positive for *Helicobacter pylori* infection comprises determining that a first patient who is positive for *Helicobacter pylori* infection has a body mass index corresponding to normal weight or overweight; determining that a second patient who is positive for *Helicobacter pylori* infection has a body mass index corresponding to obese or extremely obese; and administering to both the first patient and the second patient, for 14 days, a rifabutin-based triple therapy consisting essentially of rifabutin, amoxicillin and omeprazole or an equivalent amount of a pharmaceutically acceptable salt thereof, wherein, after treatment is complete, there is no substantial difference in the efficacy of the treatment when the treatment is administered to the first patient or the second patient. In an embodiment, the first patient has a BMI ranging from 18.50 $kg/m^2$ to 24.99 $kg/m^2$ and the second patient has a BMI ranging from 30.0 $kg/m^2$ to 34.99 $kg/m^2$. In an embodiment, the first patient has a BMI ranging from 18.50 $kg/m^2$ to 24.99 $kg/m^2$ and the second patient has a BMI ranging from 35.0 $kg/m^2$ to 39.99 $kg/m^2$. In an embodiment, the first patient has a BMI ranging from 18.50 $kg/m^2$ to 24.99 $kg/m^2$ and the second patient has a BMI above 40.00 $kg/m^2$. In an embodiment, the first patient has a BMI ranging from 25.00 $kg/m^2$ to 29.99 $kg/m^2$ and the second patient has a BMI ranging from 35.0 $kg/m^2$ to 39.99 $kg/m^2$. In an embodiment, the first patient has a BMI 25.00 $kg/m^2$ to 29.99 $kg/m^2$ and the second patient has a BMI ranging from 30.0 $kg/m^2$ to 34.99 $kg/m^2$. In an embodiment, the first patient has a BMI 25.00 $kg/m^2$ to 29.99 $kg/m^2$ and the second patient has a BMI above 40.00 $kg/m^2$. In an embodiment, the first patient and the second patient are adults. In an embodiment, the rifabutin-based triple therapy comprises a plurality of fixed-dose combination formulations which provide a total daily dose of 150 mg rifabutin, 3000 mg amoxicillin, and 120 mg omeprazole or an equivalent amount of a pharmaceutically acceptable salt thereof. In an embodiment, the administering comprises taking four fixed-dose combination formulations every 8 hours, wherein each dose of four fixed-dose combination formulations includes 50 mg rifabutin, 1,000 mg amoxicillin and 40 mg omeprazole or an equivalent amount of a pharmaceutically acceptable salt thereof. In an embodiment, each fixed-dose combination formulation comprises 12.5 mg rifabutin, 250 mg amoxicillin and 10 mg omeprazole or an equivalent amount of a pharmaceutically acceptable salt thereof. In an embodiment, each fixed-dose combination formulation is a capsule. In an embodiment, each fixed-dose combination formulation comprises a mixture of amoxicillin/rifabutin immediate release minitablets and enteric-coated omeprazole minitablets. In an embodiment, each minitablet is about 2 mm in size. In an embodiment, each fixed-dose combination formulation comprises between 36 and 40 amoxicillin/rifabutin immediate release minitablets and between 32 and 36 enteric-coated omeprazole minitablets. In an embodiment, each fixed-dose combination formulation comprises 38 amoxicillin/rifabutin immediate release minitablets and 34 enteric-coated omeprazole minitablets. In an embodiment, at least 70% by weight of the omeprazole is intestinally released after oral administration. In an embodiment, the amoxicillin is amoxicillin trihydrate. In an embodiment, the omeprazole is omeprazole magnesium. In an embodiment, the method further comprises confirming *H. pylori* eradication with a negative $^{13}C$ UBT or fecal antigen test performed ≥28 days post-therapy.

In one aspect, a method for the eradication of *Helicobacter pylori* infection in an adult comprises administering, each day for 14 days, a plurality of fixed-dose combination formulations which provide a total daily dose of 150 mg rifabutin, 3000 mg amoxicillin, and 120 mg omeprazole or an equivalent amount of a pharmaceutically acceptable salt thereof, wherein, after treatment is complete, there is no substantial difference in the efficacy of the treatment when the treatment is administered to an adult having any BMI classification, including a BMI classification of normal or healthy weight, overweight, obese or extremely obese. In an embodiment, the adult receiving the treatment has a BMI classification of normal with a BMI between 18.5 $kg/m^2$ and 24.9 $kg/m^2$. In an embodiment, the adult receiving the treatment has a BMI classification of overweight with a BMI≥25.0 $kg/m^2$. In an embodiment, the adult receiving the treatment has a BMI classification of pre-obese with a BMI between 25.0 $kg/m^2$ and 29.9 $kg/m^2$. In an embodiment, the adult receiving the treatment has a BMI classification as obese with a BMI≥30.0 $kg/m^2$. In an embodiment, the administering comprises taking four fixed-dose combination formulations every 8 hours, wherein each dose of four fixed-dose combination formulations includes 50 mg rifabutin, 1,000 mg amoxicillin and 40 mg omeprazole or an equivalent amount of a pharmaceutically acceptable salt thereof. In an embodiment, each fixed-dose combination formulation comprises 12.5 mg rifabutin, 250 mg amoxicillin and 10 mg omeprazole or an equivalent amount of a pharmaceutically acceptable salt thereof. In an embodiment, each fixed-dose combination formulation is a capsule. In an embodiment, each fixed-dose combination formulation comprises a mixture of amoxicillin/rifabutin immediate release minitablets and enteric-coated omeprazole minitablets. In an embodiment, each minitablet is about 2 mm in size. In an embodiment, each fixed-dose combination formulation comprises between 36 and 40 amoxicillin/rifabutin immediate release minitablets and between 32 and 36 enteric-coated omeprazole minitablets. In an embodiment, each fixed-dose combination formulation comprises 38 amoxicillin/rifabutin immediate release minitablets and 34 enteric-coated omeprazole minitablets. In an embodiment, at least 70% by weight of the omeprazole is intestinally released after oral administration. In an embodiment, the amoxicillin is amoxicillin trihydrate. In an embodiment, the omeprazole is omeprazole magnesium. In an embodiment, the method further comprises confirming *H. pylori* eradication with a negative $^{13}C$ UBT or fecal antigen test performed ≥28 days post-therapy.

In one aspect, a method for the eradication of *Helicobacter pylori* infection in an adult comprises administering, each day for 14 days, 12 fixed-dose combination capsules, each capsule comprising 12.5 mg rifabutin, 250 mg amoxicillin and 10 mg omeprazole or an equivalent amount of a pharmaceutically acceptable salt thereof which are present in the capsule as approximately 38 amoxicillin/rifabutin immediate release minitablets and approximately 34 enteric-coated omeprazole minitablets, wherein, after treatment is complete, there is no substantial difference in the efficacy of the treatment when the treatment is administered to an adult having any BMI classification, including a BMI classification of normal or healthy weight, overweight, obese or extremely obese. In an embodiment, the adult receiving the treatment has a BMI classification of normal with a BMI between 18.5 kg/$m^2$ and 24.9 kg/$m^2$. In an embodiment, the adult receiving the treatment has a BMI classification of overweight with a BMI≥25.0 kg/$m^2$. In an embodiment, the adult receiving the treatment has a BMI classification of pre-obese with a BMI between 25.0 kg/$m^2$ and 29.9 kg/$m^2$. In an embodiment, the adult receiving the treatment has a BMI classification as obese with a BMI≥30.0 kg/$m^2$.

In one aspect, a method for eradicating *Helicobacter pylori* infection in an obese adult preparing for bariatric surgery comprises confirming that the obese adult, having a body mass index≥30 kg/$m^2$, is infected with *Helicobacter pylori*; requesting that the obese adult orally administer, for 14 days, a plurality of fixed-dose combination formulations which provide a total daily dose of 150 mg rifabutin, 3000 mg amoxicillin, and 120 mg omeprazole or an equivalent amount of a pharmaceutically acceptable salt thereof; and confirming that the *Helicobacter pylori* infection has been eradicated. In an embodiment, the administering comprises taking four fixed-dose combination formulations every 8 hours, wherein each dose of four fixed-dose combination formulations includes 50 mg rifabutin, 1,000 mg amoxicillin and 40 mg omeprazole or an equivalent amount of a pharmaceutically acceptable salt thereof. In an embodiment, each fixed-dose combination formulation comprises 12.5 mg rifabutin, 250 mg amoxicillin and 10 mg omeprazole or an equivalent amount of a pharmaceutically acceptable salt thereof. In an embodiment, each fixed-dose combination formulation is a capsule. In an embodiment, each fixed-dose combination formulation comprises a mixture of amoxicillin/rifabutin immediate release minitablets and enteric-coated omeprazole minitablets. In an embodiment, each minitablet is about 2 mm in size. In an embodiment, each fixed-dose combination formulation comprises between 36 and 40 amoxicillin/rifabutin immediate release minitablets and between 32 and 36 enteric-coated omeprazole minitablets. In an embodiment, each fixed-dose combination formulation comprises 38 amoxicillin/rifabutin immediate release minitablets and 34 enteric-coated omeprazole minitablets. In an embodiment, at least 70% by weight of the omeprazole is intestinally released after oral administration. In an embodiment, the amoxicillin is amoxicillin trihydrate. In an embodiment, the omeprazole is omeprazole magnesium. In an embodiment, the confirming that the obese adult is infected with *Helicobacter pylori* is carried out with a $^{13}C$ UBT or fecal antigen test. In an embodiment, the confirming that the *Helicobacter pylori* infection has been eradicated is carried out with a $^{13}C$ UBT or fecal antigen test performed ≥28 days post-therapy.

In one aspect, a method for preparing an obese adult for bariatric surgery comprises testing the obese adult having a body mass index≥30 kg/$m^2$ for infection with *Helicobacter pylori*, and if the obese adult is confirmed to have *Helicobacter pylori*, providing the obese adult with a plurality of fixed-dose combination formulations which provide a total daily dose of 150 mg rifabutin, 3000 mg amoxicillin, and 120 mg omeprazole or an equivalent amount of a pharmaceutically acceptable salt thereof for a total of 14 days; and confirming that the *Helicobacter pylori* infection has been eradicated. In an embodiment, four fixed-dose combination formulations are administered to the obese adult every 8 hours, wherein each dose of four fixed-dose combination formulations includes 50 mg rifabutin, 1,000 mg amoxicillin and 40 mg omeprazole or an equivalent amount of a pharmaceutically acceptable salt thereof. In an embodiment, each fixed-dose combination formulation comprises 12.5 mg rifabutin, 250 mg amoxicillin and 10 mg omeprazole or an equivalent amount of a pharmaceutically acceptable salt thereof. In an embodiment, each fixed-dose combination formulation is a capsule. In an embodiment, each fixed-dose combination formulation comprises a mixture of amoxicillin/rifabutin immediate release minitablets and enteric-coated omeprazole minitablets. In an embodiment, each minitablet is about 2 mm in size. In an embodiment, each fixed-dose combination formulation comprises between 36 and 40 amoxicillin/rifabutin immediate release minitablets and between 32 and 36 enteric-coated omeprazole minitablets. In an embodiment, each fixed-dose combination formulation comprises 38 amoxicillin/rifabutin immediate release minitablets and 34 enteric-coated omeprazole minitablets. In an embodiment, at least 70% by weight of the omeprazole is intestinally released after oral administration. In an embodiment, the amoxicillin is amoxicillin trihydrate. In an embodiment, the omeprazole is omeprazole magnesium. In an embodiment, the confirming that the obese adult is infected with *Helicobacter pylori* is carried out with a $^{13}C$ UBT or fecal antigen test. In an embodiment, the confirming that the *Helicobacter pylori* infection has been eradicated is carried out with a $^{13}C$ UBT or fecal antigen test performed ≥28 days post-therapy.

In one aspect, a method of eradicating *Helicobacter pylori* infection in an obese adult during the pre-operative phase of a bariatric surgery intervention comprises testing the obese adult having a body mass index≥30 kg/m 2 for infection with *Helicobacter pylori*, and if the obese adult is confirmed to have *Helicobacter pylori*, providing the obese adult with a plurality of fixed-dose combination formulations which provide a total daily dose of 150 mg rifabutin, 3000 mg amoxicillin, and 120 mg omeprazole or an equivalent amount of a pharmaceutically acceptable salt thereof for a total of 14 days; and confirming that the *Helicobacter pylori* infection has been eradicated. In an embodiment, four fixed-dose combination formulations are administered to the obese adult every 8 hours, wherein each dose of four fixed-dose combination formulations includes 50 mg rifabutin, 1,000 mg amoxicillin and 40 mg omeprazole or an equivalent amount of a pharmaceutically acceptable salt thereof. In an embodiment, each fixed-dose combination formulation comprises 12.5 mg rifabutin, 250 mg amoxicillin and 10 mg omeprazole or an equivalent amount of a pharmaceutically acceptable salt thereof. In an embodiment, each fixed-dose combination formulation is a capsule. In an embodiment, each fixed-dose combination formulation comprises a mixture of amoxicillin/rifabutin immediate release minitablets and enteric-coated omeprazole minitablets. In an embodiment, each minitablet is about 2 mm in size. In an embodiment, each fixed-dose combination formulation comprises between 36 and 40 amoxicillin/rifabutin immediate release minitablets and between 32 and 36 enteric-coated omeprazole minitablets. In an embodiment, each fixed-dose combination formulation comprises 38 amoxicillin/rifabutin immediate release minitablets and 34 enteric-coated omeprazole minitablets. In an embodiment, at least 70% by weight of the omeprazole is intestinally released after oral administration. In an embodiment, the amoxicillin is amoxicillin trihydrate. In an embodiment, the omeprazole is omeprazole magnesium. In an embodiment, the confirming that the obese adult is infected with *Helicobacter pylori* is carried out with a $^{13}C$ UBT or fecal antigen test. In an embodiment, the confirming that the *Helicobacter pylori* infection has been eradicated is carried out with a $^{13}C$ UBT or fecal antigen test performed ≥28 days post-therapy.

A fixed-dose combination formulation comprising 12.5 mg rifabutin, 250 mg amoxicillin and 10 mg omeprazole or an equivalent amount of a pharmaceutically acceptable salt thereof for use in the treatment of *H. pylori* infection in an obese patient, wherein the obese patient has a body mass index≥30 kg/m$^2$.

A fixed-dose combination formulation comprising 12.5 mg rifabutin, 250 mg amoxicillin and 10 mg omeprazole or an equivalent amount of a pharmaceutically acceptable salt thereof for use in the treatment of *H. pylori* infection in an obese patient preparing for bariatric surgery, wherein the obese patient has a body mass index≥30 kg/m$^2$.

A fixed-dose combination formulation comprising 12.5 mg rifabutin, 250 mg amoxicillin and 10 mg omeprazole or an equivalent amount of a pharmaceutically acceptable salt thereof for use as a medicament in the treatment of *H. pylori* infection in an obese patient having a body mass index≥30 kg/m$^2$.

A fixed-dose combination formulation comprising 12.5 mg rifabutin, 250 mg amoxicillin and 10 mg omeprazole or an equivalent amount of a pharmaceutically acceptable salt thereof for use as a medicament in the treatment of *H. pylori* infection in an obese patient preparing for bariatric surgery, wherein the obese patient has a body mass index≥30 kg/m$^2$.

A fixed-dose combination formulation comprising 12.5 mg rifabutin, 250 mg amoxicillin and 10 mg omeprazole or an equivalent amount of a pharmaceutically acceptable salt thereof in preparation of a medicament in the treatment of *H. pylori* infection in an obese patient having a body mass index≥30 kg/m$^2$.

A fixed-dose combination formulation comprising 12.5 mg rifabutin, 250 mg amoxicillin and 10 mg omeprazole or an equivalent amount of a pharmaceutically acceptable salt thereof in preparation of a medicament in the treatment of *H. pylori* infection in an obese patient preparing for bariatric surgery, wherein the obese patient has a body mass index≥30 kg/m$^2$.

BRIEF DESCRIPTION OF THE DRAWINGS

The presently disclosed embodiments will be further explained with reference to the drawings.

Figure 1:
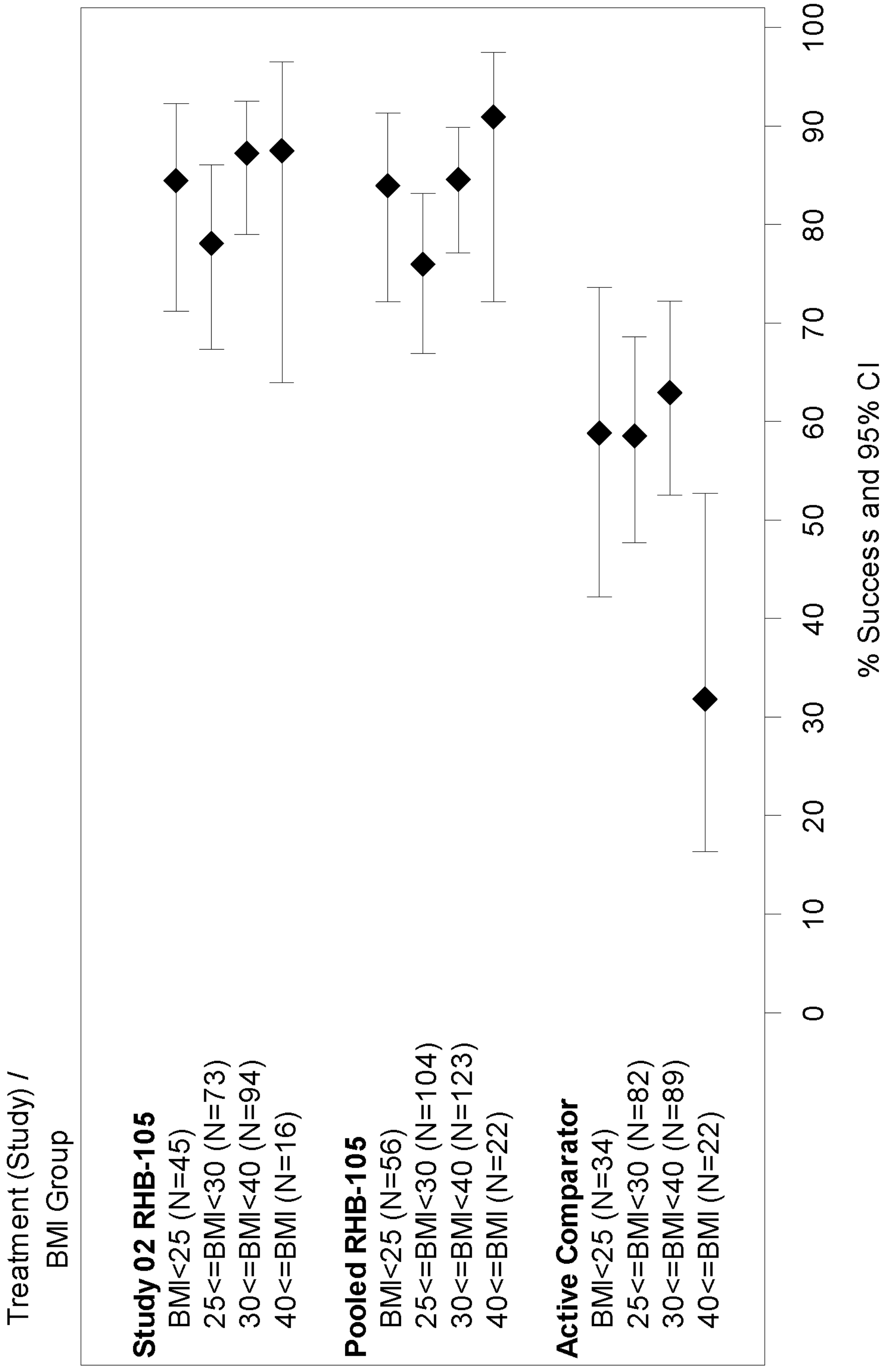
FIG. 1 shows a Forest Plot in the intent-to-treat (ITT) population for two studies that compared the success (%) of *H. pylori* eradication by three (3) body mass index subgroups. Solid circles represent hazard ratios (95% CI).

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

Obesity is most often classified using body mass index (BMI) (WHO classification):

| BMI, kg/m$^2$ | WHO classification |
|---|---|
| Below 18.5 | Underweight |
| 18.50-24.99 | Normal or Healthy Weight |
| 25.0-29.99 | Overweight |
| 30.00-34.99 | Obese class I |
| 35.00-39.99 | Obese class II |
| 40.00 or greater | Obese class III (morbidly obese, extremely obese) |

As used herein, empiric triple *H. pylori* therapy consists of a proton pump inhibitor (PPI) plus two antibiotics (amoxicillin with clarithromycin or metronidazole)

As used herein, empiric concomitant quadruple *H. pylori* therapy consists of a PPI plus three antibiotics (amoxicillin, clarithromycin, and metronidazole.

As used herein, a “fixed-dose combination” is two or more drugs contained in a single dosage form, such as a capsule or tablet.

As used herein, “did not work as well”, means that the same exact therapy (e.g., same drugs, same dosage strengths of drugs, same dosing schedule of drugs, and same amount of treatment in days/weeks) was inferior by at least 15% in a patient having a BMI in the overweight/obese category as compared to a patient having a BMI in the normal category. In an embodiment, “did not work as well”, means that the same exact therapy (e.g., same drugs, same dosage strengths of drugs, same dosing schedule of drugs, and same amount of treatment in days/weeks) was inferior by at least 20% in a patient having a BMI in the overweight/obese category as compared to a patient having a BMI in the normal category. In an embodiment, “did not work as well”, means that the same exact therapy (e.g., same drugs, same dosage strengths of drugs, same dosing schedule of drugs, and same amount of treatment in days/weeks) was inferior by at least 25% in a patient having a BMI in the overweight/obese category as compared to a patient having a BMI in the normal category.

As used herein, "substantially equivalent", means that the eradication rate of a patient within any BMI classification as compared to another BMI classification is within 10% on the same exact therapy (e.g., same drugs, same dosage strengths of drugs, same dosing schedule of drugs, and same amount of treatment in days/weeks) and thus is not substantially different.

As used herein, the intent-to-treat (ITT) population (also known as full analysis set (FAS) population) includes all subjects who took at least one dose of study drug.

As used herein, the modified intent-to-treat (mITT) population includes all subjects who took at least one dose of study drug and who returned for follow up test of cure.

Rifabutin-based triple therapy for treating *H. pylori* infection in adults is marketed in the U.S. by RedHill Biopharma Inc. and under the brand name Talicia®. Talicia® is a fixed-dose combination (FDC) capsule comprising omeprazole magnesium, amoxicillin and rifabutin for oral administration and is described, for example, in U.S. Pat. Nos. 9,050,263; 9,498,445; 9,603,806; and 10,238,606, all of which are specifically incorporated by reference.

Talicia® delayed-release capsules contain a mixture of amoxicillin/rifabutin immediate release minitablets and enteric-coated omeprazole minitablets. Each minitablet is a compressed tablet with a typical diameter of one to four millimeters, and more preferably about 2.45 mm±0.15 mm. Early clinical batches were performed on a mini-encapsulator, which was semi-automatic. The capsules were filled by allowing an equal weight of each type of minitablet to be encapsulated, but the number of each type of minitablet was not controlled. To provide additional control over the actual number of each type of minitablet encapsulated, rather than just equivalent weights, the equipment selected for use in the later clinical and production batches employs a dosing wheel to ensure a maximum of 38 rifabutin/amoxicillin minitablets, and 34 delayed-release omeprazole minitablets, are encapsulated. The Talicia® delayed-release capsules are filled using an encapsulator fitted with two minitablet hoppers and a microtablet dosing unit. The unit is comprised of a wheel with a predefined number of holes, the dimensions of which are dictated by the size of the minitablets. The minitablets enter into the wheel holes by means of a vacuum and a brush eliminates excess minitablets. The wheel rotates, the vacuum is cut off and the minitablets fall down into the drum. One row of rifabutin/amoxicillin minitablets are released into each gelatin capsule (along with the contents of the second wheel, containing the delayed-release omeprazole minitablets). During the filling process, some holes could be empty or minitablets might not be released into the capsule if the tablet becomes stuck. As a result, filled capsules have a maximum of 38 amoxicillin/rifabutin minitablets and 34 omeprazole minitablets, but may actually have less. The target weight for each Talicia® capsule is calculated on a per batch basis, taking into account the average weight of the minitablets used. In an embodiment, each FDC of the present invention comprises between 36 and 40 amoxicillin/rifabutin immediate release minitablets and between 32 and 36 enteric-coated omeprazole minitablets, and more preferably 38 amoxicillin/rifabutin immediate release minitablets and 34 enteric-coated omeprazole minitablets.

Omeprazole magnesium, a proton pump inhibitor, is included in the delayed-release component of the capsule, and amoxicillin and rifabutin, antibacterial drugs, are included in the immediate-release component of the capsule. Each delayed-release capsule, which is a fixed-dose combination formulation, contains:

omeprazole 10 mg (equivalent to 10.3 mg of omeprazole magnesium)

amoxicillin 250 mg (equivalent to 286.9 mg of amoxicillin trihydrate)

rifabutin 12.5 mg

Each Talicia® delayed-release capsule further contains the following inactive ingredients: crospovidone, FD&C Red 3, FD&C Yellow 6, gelatin, hydroxypropyl cellulose, hypromellose, magnesium stearate, mannitol-starch, methacrylic acid copolymer, meglumine, pregelatinized starch, silica, sodium bicarbonate, sodium lauryl sulfate, talc, titanium dioxide and triethyl citrate.

According to its approved use, four (4) Talicia® capsules should be administered every 8 hours for 14 days with food and a full glass of water (8 ounces). Each dose (4 capsules) of Talicia® includes rifabutin 50 mg, amoxicillin 1,000 mg and omeprazole 40 mg.

Omeprazole Magnesium

Omeprazole magnesium is a white to off-white powder with a melting point with degradation at 200° C. The salt is slightly soluble (0.25 mg/mL) in water at 25° C., and it is soluble in methanol. Omeprazole magnesium is 5-methoxy-2-[[(4-methoxy-3,5-dimethyl-2-pyridyl) methyl] sulfinyl] benzimidazole, (RS) magnesium salt (2:1). Omeprazole magnesium has a molecular formula of $(C_{17}H_{19}N_3O_3S)_2$ Mg, and a molecular weight of 713.12. The structural formula is:

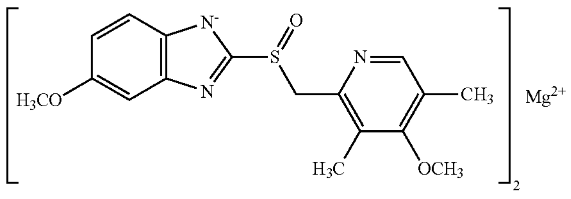

Amoxicillin

Amoxicillin is a semisynthetic antibacterial drug, an analog of ampicillin Chemically it is (2S,5R,6R)-6-[(R)-(−)-2-amino-2-(p-hydroxyphenyl)acetamido]-3,3-dimethyl-7-oxo-4-thia-1-azabicyclo[3.2.0] heptane-2-carboxylic acid trihydrate. Amoxicillin has a molecular formula of $C_{16}H_{19}N_3O_5S \cdot 3H_2O$, and a molecular weight of 419.45. The structural formula is:

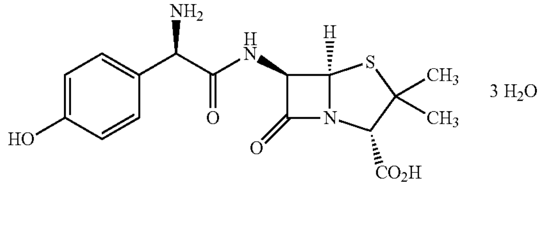 [SMILES: CC1(C)S[C@@H]2[C@H](NC(=O)[C@H](N)c3ccc(O)cc3)C(=O)N2[C@H]1C(=O)O]

Amoxicillin is a broad antimicrobial beta-lactam that inhibits the synthesis of the bacterial cell wall in replicating bacteria. Amoxicillin is bactericidal for both gram-positive and gram-negative bacteria and is destroyed by beta-lactamase produced from both types of bacteria.

Rifabutin

Rifabutin is a red-violet powder soluble in chloroform and methanol, sparingly soluble in ethanol, and very slightly soluble in water (0.19 mg/mL). Its log P value (the base 10 logarithm of the partition coefficient between n-octanol and water) is 3.2 (n-octanol/water).

Rifabutin is (9S,12E,14S,15R,16S,17R,18R,19R,20S,21S,22E,24Z)-6-16,18,20-tetrahydroxy-1'-isobutyl-14-methoxy-7,9,15,17,19,21,25-heptamethylspiro [9,4-(epoxypentadeca[1,11,13]trienimino)-2H-furo[2',3':7,8]naphth[1,2-d] imidazole-2,4'-piperidine]-5,10,26-(3H,9H)-trione-16-acetate. Rifabutin has a molecular formula of $C_{46}H_{62}N_4O_{11}$, and a molecular weight of 847.02. The structural formula is:

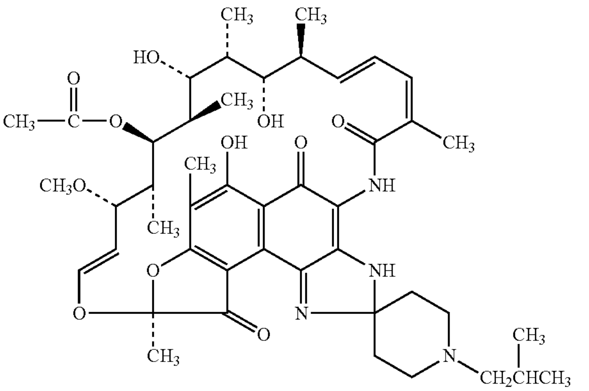

The effectiveness and safety of Talicia® were evaluated in a randomized, double-blind, controlled study of Talicia® in treatment-naïve *H. pylori*-positive adult patients complaining of epigastric pain/discomfort (Study 1). *H. pylori* infection at baseline was defined as positive by $^{13}C$ urea breath test (UBT) and follow-up upper endoscopy (culture, histology, or *Campylobacter*-like organism test). Patients were randomized 1:1 to Talicia® or control (total daily dose of amoxicillin 3000 mg and omeprazole 120 mg) administered for 14 consecutive days. The trial was performed in the U.S and designed to evaluate the added contribution of rifabutin to the Talicia® triple combination.

*H. pylori* eradication was confirmed with a negative $^{13}C$ UBT or fecal antigen test performed ≥28 days post-therapy and suspended PPI. Patients with negative test results were considered treatment successes. Patients who tested positive for *H. pylori* infection were considered treatment failures, and patients with indeterminate, not assessable, or missing results from the test of cure visits underwent a repeat $^{13}C$ UBT test. Persistent indeterminate results and patients without any $^{13}C$ UBT or fecal antigen test after baseline were considered as treatment failures.

*H. pylori* eradication rates are shown in Table 1. The difference in response rates between Talicia® and the control was 26.1% (95% CI; 18.0, 34.1).

TABLE 1

Eradication Rates of *H. pylori* in Study 1

| *H. pylori* Eradication | ITT Population[a] Talicia ® N = 228 (%) | Control N = 227 (%) |
|---|---|---|
| Success | 191 (83.8) | 131 (57.7) |
| Failure | 37 (16.2)[b] | 96 (42.3) |
| P-value | <0.0001 | |

[a]The Intent to Treat (ITT) population included all randomized patients who received at least one dose of study drug.

[b]Of those subjects classified as treatment failures, all but one subject in the Talicia ® group were positive by $^{13}C$ UBT; this one subject was classified as a treatment failure due to a missing post-baseline test result.

A randomized, double-blind, placebo-controlled study of Talicia® in *H. pylori*-positive adult patients complaining of epigastric pain/discomfort (Study 2) was performed in the U.S. and provided supportive evidence for the efficacy of Talicia® for the treatment of *H. pylori* infection; 77 patients taking Talicia® and 41 patients taking placebo were included in the ITT population, with an eradication rate of 76.6% (95% CI; 66.0%, 84.7%) for the Talicia®-treated patients compared to 2.4% for the placebo-treated patients. Eleven patients in the Talicia® arm and four patients in the placebo arm were classified as treatment failures due to missing $^{13}C$ UBT results at the test-of-cure visit.

In the past, medical professionals have described the need for a patient-tailored *H. pylori* eradication protocol for obese patients about to undergo bariatric surgery to improve the eradication rate, which is reportedly insufficient compared with that in the non-obese population. Abdullahi et al. conducted a pilot study to evaluate whether body mass index (BMI) might influence the success rate of *H. pylori* eradication (OBES SURG (2008) 18: 1450-1454). In that pilot study, eighty-one nondiabetic naïve *H. pylori*-positive patients were divided into two groups according to their BMI, with 41 in the control group (normal BMI) and 40 in the overweight/obese group (BMI, of ≥25). Both groups were given a triple therapy consisting of pantoprazole 40 mg, as proton pump inhibitor, for 2 weeks plus amoxicillin 1 g t.i.d, and clarithromycin 250 mg t.i.d, as antibacterial agents, for the first week of treatment. Eradication was confirmed by the $^{13}C$-urea breath test at 3 months. In that pilot study, successful eradication was observed in 55.0% of the overweight/obese group (Body Mass Index, BMI, of ≥25) compared with 85.4% in the normal BMI group. [p<0.005; odds ratio (OR): 4.77; 95% confidence interval (CI): 1.64-13.87].

FDA Phase III studies may or may not establish that a drug works to treat a particular disease or condition. Moreover, prior to completion and evaluation of Phase III, a person of skill in the art would not necessarily understand that the drug is useful for treatment of the disease or condition or that the drug can be administered "as-is" to any patient regardless of BMI.

Data was pooled from the two above-mentioned Phase 3 clinical studies (Study 1 and Study 2) assessing *H. pylori* eradication with RHB-105 (an 'all-in-one' low-dose rifabutin therapy providing 50 mg rifabutin, 1,000 mg amoxicillin, and 40 mg omeprazole) vs an active comparator of a high dose PPI-amoxicillin (1,000 mg amoxicillin and 40 mg omeprazole) q8h for 14 days. Treatment naïve subjects with confirmed *H. pylori* infection were treated and eradication verified using $^{13}C$ UBT (urea breath test) at least 4 weeks post-therapy as a test-of-cure. An analysis was performed on the pooled Intent-to-Treat (ITT) population and calculated eradication rates based upon BMI cut points: ≤30 kg/m 2 representing overweight and below, obese ≥30 kg/m 2 and <40 kg/$m^2$, and extremely obese ≥40 kg/$m^2$ BMI measures (Table 2) and BMI cut points: <40 kg/$m^2$ (normal, overweight and obese) and extremely obese ≥40 kg/$m^2$ BMI measures (Table 3). A comparison was made between the RHB-105 and the active comparator treatment groups using pooled ITT and other analyses.

In the pooled analysis, there were 532 evaluable subjects (305 pooled RHB-105 treatment group and 227 in the active comparator group). The mean age was 45.9 vs. 47.2 years. Other characteristics were generally similar with and a mean BMI of 30.4 kg/$m^2$ vs. 30.9 kg/$m^2$. Looking more closely at eradication rates based upon 3 BMI subgroups (Table 2), pooled RHB-105 rates were 82.4%, 84.6%, 90.9% for BMI≤30, >30 and <40, ≥40 vs 58.6%, 62.9%, 31.8% (Active Comparator), respectively. Looking more closely at eradication rates based upon 2 BMI subgroups (Table 3), pooled RHB-105 rates were 81.3% and 90.9% for BMI<40, ≥40 vs 60.5% and 31.8% (Active Comparator), respectively. RHB-105 eradication was statistically significant for all BMI subgroups over the active comparator (P<0.0001). As such, BMI does not appear to influence eradication rates among the RHB-105 group while there was a ~50%-60% drop in the active comparator eradication for the highest BMI group.

TABLE 2

BMI Influence on *H. pylori* Eradication Success Rate (ITT) - 3 BMI Subgroups

| BMI Group | Assessment | Study RHB-105-02 RHB-105 (N = 228) | Pooled RHB-105 (N = 305) | Study RHB-105-02 Active Comparator (N = 227) |
|---|---|---|---|---|
| BMI <= 30 | n | 118 | 153 | 116 |
| | Treatment Success | 95 (80.5%) | 126 (82.4%) | 68 (58.6%) |
| | 95% CI | 72.4-86.6 | 75.5-87.6 | 49.5-67.2 |
| 30 < BMI < 40 | n | 94 | 123 | 89 |
| | Treatment Success | 82 (87.2%) | 104 (84.6%) | 56 (62.9%) |
| | 95% CI | 79.0-92.5 | 77.1-89.9 | 52.5-72.2 |
| BMI >= 40 | n | 16 | 22 | 22 |
| | Treatment Success | 14 (87.5%) | 20 (90.9%) | 7 (31.8%) |
| | 95% CI | 64.0-96.5 | 72.2-97.5 | 16.4-52.7 |

TABLE 3

BMI Influence on *H. pylori* Eradication Success Rate (ITT) - 2 BMI Subgroups

| BMI Group | Assessment | Study RHB-105-02 RHB-105 (N = 228) | Pooled RHB-105 (N = 305) | Study RHB-105-02 Active Comparator (N = 227) |
|---|---|---|---|---|
| BMI < 40 | n | 212 | 283 | 205 |
| | Treatment Success | 177 (83.5%) | 230 (81.3%) | 124 (60.5%) |
| | 95% CI | 77.9-87.9 | 76.3-85.4 | 53.7-66.9 |
| 40 <= BMI | n | 16 | 22 | 22 |
| | Treatment Success | 14 (87.5%) | 20 (90.9%) | 7 (31.8%) |
| | 95% CI | 64.0-96.5 | 72.2-97.5 | 16.4-52.7 |

Figure 2:
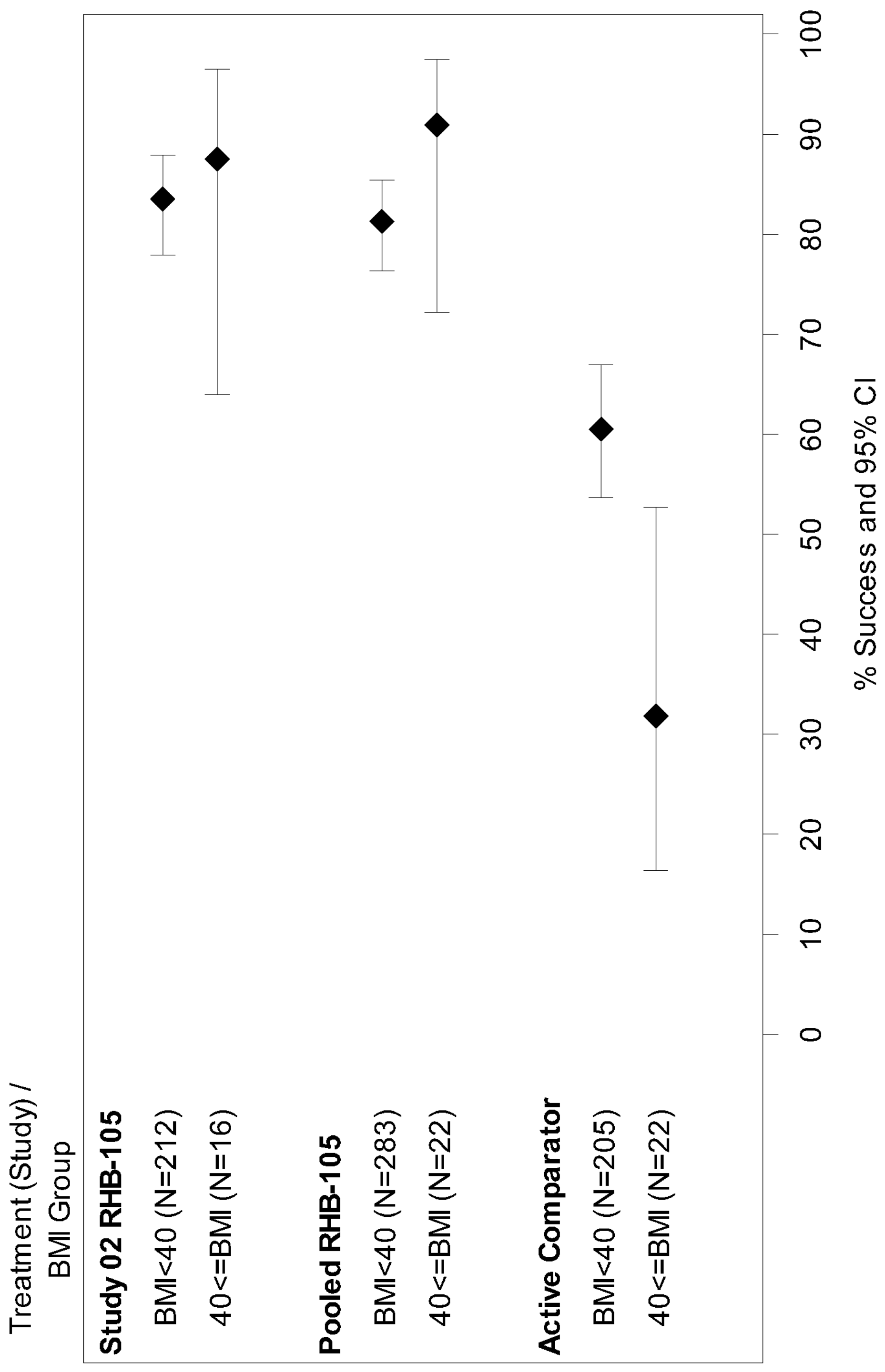
FIG. 2 shows a Forest Plot in the intent-to-treat (ITT) population for two studies that compared the success (%) of *H. pylori* eradication by two (2) body mass index subgroups. Solid circles represent hazard ratios (95% CI).

FIG. 1 shows a Forest Plot in the intent-to-treat (ITT) population for two studies that compared the success (%) of *H. pylori* eradication by three (3) body mass index subgroups. Solid circles represent hazard ratios (95% CI). FIG. 2 shows a Forest Plot in the intent-to-treat (ITT) population for two studies that compared the success (%) of *H. pylori* eradication by two (2) body mass index subgroups. Solid circles represent hazard ratios (95% CI).

Eradication rates of the Active Comparator were greatly affected by increase in BMI. Rifabutin mitigated the BMI influenced failure of eradication seen with the active comparator for extremely obese subjects. The addition of low-dose rifabutin demonstrated a statistically significant improvement and clinically meaningful eradication vs the active comparator. RHB-105 may serve as a first line empiric treatment of *H. pylori* infection and may be useful in eradication of *H. pylori* infection regardless of BMI status.

What is claimed is:

1. A method of treating patients who are positive for *Helicobacter pylori* infection comprising:

determining that a first patient who is positive for *Helicobacter pylori* infection has a body mass index corresponding to normal weight or overweight;

determining that a second patient who is positive for *Helicobacter pylori* infection has a body mass index corresponding to obese or extremely obese; and administering to both the first patient and the second patient, for 14 days three times a day with food, four fixed-dose combination formulations which provide a total daily dose of 150 mg rifabutin, 3,000 mg amoxicillin, and 120 mg omeprazole or an equivalent amount of a pharmaceutically acceptable salt thereof, wherein each fixed-dose combination formulation comprises between 36 and 40 immediate release minitablets comprising both amoxicillin and rifabutin, and between 32 and 36 enteric-coated omeprazole minitablets, and wherein, after treatment is complete, there is no substantial difference in the efficacy of the treatment when the treatment is administered to the first patient or the second patient.

2. The method of claim 1, wherein the first patient has a BMI ranging from 18.50 kg/$m^2$ to 24.99 kg/$m^2$ and the second patient has a BMI ranging from 30.0 kg/$m^2$ to 34.99 kg/$m^2$.

3. The method of claim 1, wherein the first patient has a BMI ranging from 18.50 kg/$m^2$ to 24.99 kg/$m^2$ and the second patient has a BMI ranging from 35.0 kg/$m^2$ to 39.99 kg/$m^2$.

4. The method of claim 1, wherein the first patient has a BMI ranging from 18.50 kg/$m^2$ to 24.99 kg/$m^2$ and the second patient has a BMI above 40.00 kg/$m^2$.

5. The method of claim 1, wherein the first patient has a BMI ranging from 25.00 kg/$m^2$ to 29.99 kg/$m^2$ and the second patient has a BMI ranging from 35.0 kg/$m^2$ to 39.99 kg/$m^2$.

6. The method of claim 1, wherein the first patient has a BMI 25.00 kg/$m^2$ to 29.99 kg/$m^2$ and the second patient has a BMI ranging from 30.0 kg/$m^2$ to 34.99 kg/$m^2$.

7. The method of claim 1, wherein the first patient has a BMI 25.00 kg/$m^2$ to 29.99 kg/$m^2$ and the second patient has a BMI above 40.00 kg/$m^2$.

8. The method of claim 1, wherein the administering to both the first patient and the second patient comprises taking four fixed-dose combination formulations every 8 hours, wherein each dose of four fixed-dose combination formulations includes 50 mg rifabutin, 1,000 mg amoxicillin and 40 mg omeprazole or an equivalent amount of a pharmaceutically acceptable salt thereof.

9. The method of claim 1, wherein each fixed-dose combination formulation comprises 12.5 mg rifabutin, 250 mg amoxicillin and 10 mg omeprazole or an equivalent amount of a pharmaceutically acceptable salt thereof.

10. The method of claim 1, wherein each fixed-dose combination formulation is a capsule.

11. The method of claim 1, wherein each fixed-dose combination formulation comprises a mixture of amoxicillin and rifabutin immediate release minitablets and enteric-coated omeprazole minitablets.

12. The method of claim 11, wherein the immediate release minitablets and the enteric-coated omeprazole minitablets are each about 2 mm in size.

13. The method of claim 11, wherein each fixed-dose combination formulation comprises 38 of the immediate release minitablets and 34 of the enteric-coated minitablets.

14. The method of claim 1, wherein at least 70% by weight of the omeprazole is intestinally released after oral administration.

15. The method of claim 1, wherein the amoxicillin is amoxicillin trihydrate.

16. The method of claim 1, wherein the omeprazole is omeprazole magnesium.

17. The method of claim 1, further comprising confirming *H. pylori* eradication with a negative $^{13}C$ UBT or fecal antigen test performed ≥28 days post-therapy.

18. The method of claim 1, wherein the second patient who tested positive for *Helicobacter pylori* infection is obese with a BMI above 30.00 kg/$m^2$ and is preparing for bariatric surgery.

19. A method of treating *Helicobacter pylori* infection comprising:
- determining that a patient is positive for *Helicobacter pylori* infection and has a body mass index corresponding to obese or extremely obese; and
- administering to the patient for 14 days three times a day with food a rifabutin-based triple therapy comprising a plurality of fixed-dose combination formulations which provide a total daily dose of 150 mg rifabutin, 3,000 mg amoxicillin, and 120 mg omeprazole or an equivalent amount of a pharmaceutically acceptable salt thereof,
  - wherein each fixed-dose combination formulation comprises between 36 and 40 immediate release minitablets comprising both amoxicillin and rifabutin, and between 32 and 36 enteric-coated omeprazole minitablets.

* * * * *